(12) United States Patent
Kunkov

(10) Patent No.: US 10,743,959 B2
(45) Date of Patent: Aug. 18, 2020

(54) DEVICE AND METHODS OF NEEDLE CALIBRATION

(71) Applicant: EM Device Lab, Inc., Austin, TX (US)

(72) Inventor: Sergey Kunkov, Woodbury, NY (US)

(73) Assignee: EM DEVICE LAB, INC., Austin, TX (US)

( * ) Notice: Subject to any disclaimer, the term of this patent is extended or adjusted under 35 U.S.C. 154(b) by 107 days.

(21) Appl. No.: 16/003,878

(22) Filed: Jun. 8, 2018

(65) Prior Publication Data

US 2019/0105123 A1 Apr. 11, 2019

Related U.S. Application Data

(60) Provisional application No. 62/516,728, filed on Jun. 8, 2017.

(51) Int. Cl.

| | |
|---|---|
| *G01B 5/14* | (2006.01) |
| *A61B 90/00* | (2016.01) |
| *G01B 3/00* | (2006.01) |
| *G01B 5/00* | (2006.01) |
| *A61B 17/34* | (2006.01) |
| *G01B 5/18* | (2006.01) |
| *G01B 21/04* | (2006.01) |
| *A61B 17/00* | (2006.01) |
| *A61B 34/10* | (2016.01) |

(52) U.S. Cl.
CPC .......... *A61B 90/06* (2016.02); *A61B 17/3401* (2013.01); *A61B 17/3403* (2013.01); *G01B 3/006* (2013.01); *G01B 5/0004* (2013.01); *G01B 5/18* (2013.01); *G01B 21/042* (2013.01); *G01B 21/047* (2013.01); *A61B 2017/00725* (2013.01); *A61B 2017/3413* (2013.01); *A61B 2017/3492* (2013.01); *A61B 2034/105* (2016.02); *A61B 2090/034* (2016.02); *A61B 2090/062* (2016.02); *A61B 2090/378* (2016.02); *A61B 2560/0223* (2013.01)

(58) Field of Classification Search
CPC .......................... A61B 90/06; A61B 2090/061
USPC .................................................... 33/512, 832
See application file for complete search history.

(56) References Cited

U.S. PATENT DOCUMENTS

| | | | | |
|---|---|---|---|---|
| 4,760,847 | A * | 8/1988 | Vaillancourt | A61M 39/0208 128/907 |
| 5,253,653 | A * | 10/1993 | Daigle | A61M 25/09 600/434 |
| 5,810,841 | A * | 9/1998 | McNeirney | A61B 90/13 606/130 |
| 6,450,976 | B2 * | 9/2002 | Korotko | A61B 5/1076 33/512 |
| 7,562,458 | B1 * | 7/2009 | Clark, Jr. | A61G 7/018 33/333 |
| 8,572,860 | B2 * | 11/2013 | Fritzinger | A61B 90/06 33/512 |
| 9,554,785 | B2 * | 1/2017 | Walters | A61B 17/0057 |

(Continued)

*Primary Examiner* — George B Bennett
(74) *Attorney, Agent, or Firm* — Trop, Pruner & Hu, P.C.

(57) ABSTRACT

In some embodiments, a device may include a tube having substantially cylindrical body defining an enclosure and having an open end. The tube may include measurement units printed along at least one side. The device may further include a stopper element releasably coupled to the open end of the cylindrical body and configured to selectively engage a needle to mark a length of the needle.

20 Claims, 18 Drawing Sheets

(56) References Cited

U.S. PATENT DOCUMENTS

| | | | | |
|---|---|---|---|---|
| 2005/0138826 A1* | 6/2005 | Hsieh | ............... | G01V 9/00 33/542 |
| 2008/0104855 A1* | 5/2008 | Kim | ............... | G01B 3/28 33/836 |
| 2013/0247403 A1* | 9/2013 | Hayashida | ............... | G01B 5/207 33/505 |

* cited by examiner

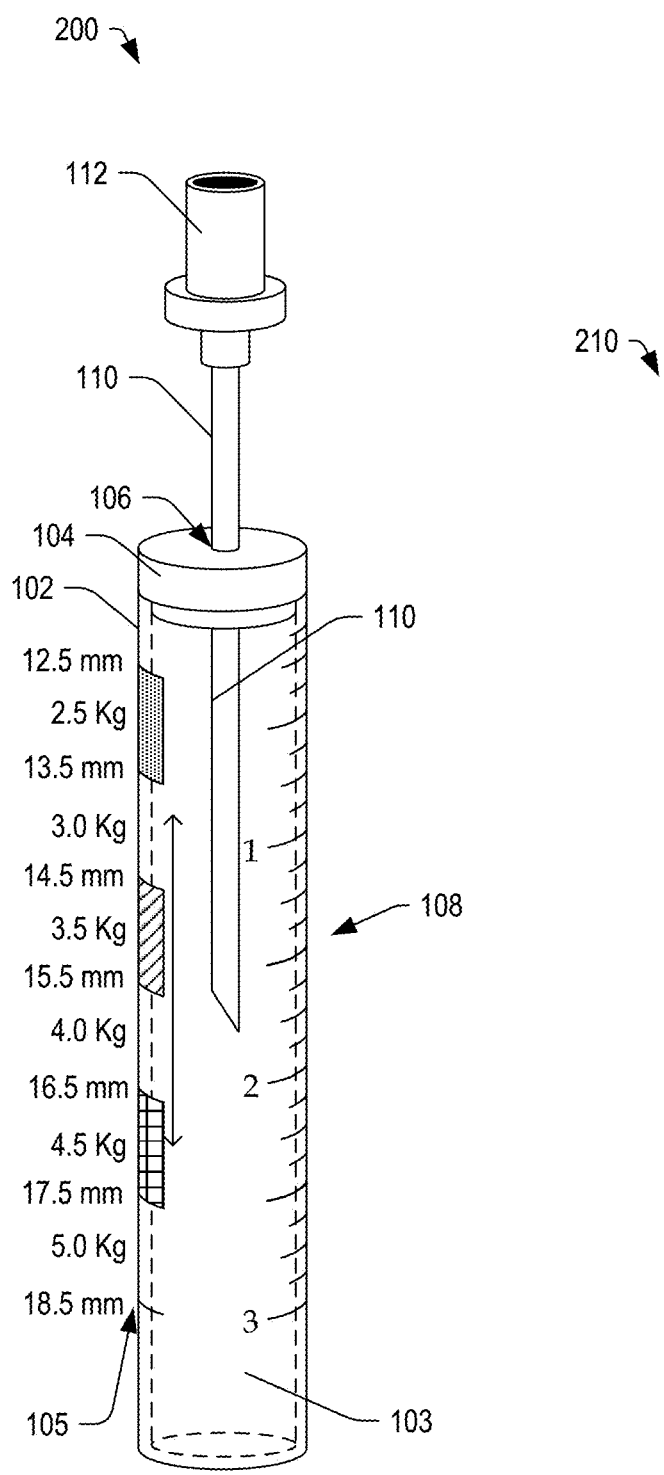
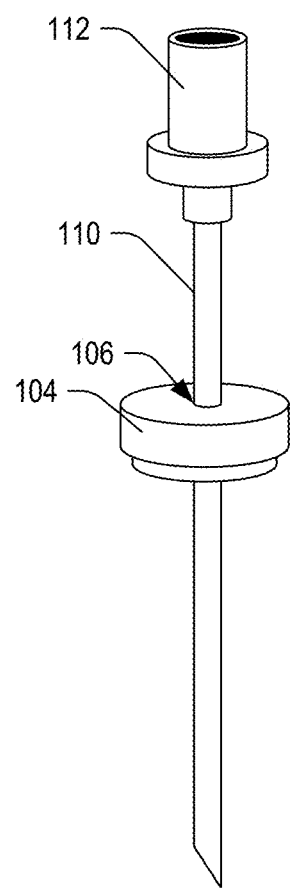
*FIG. 2A*  *FIG. 2B*

A. Ultrasonic spinal evaluation from a longitudinal view
B. Ultrasonic spinal evaluation from a transverse view
C. Perspective view of probe orientation from the longitudinal view
D. Perspective view of probe orientation from the transverse view

1100

1300

DEVICE AND METHODS OF NEEDLE CALIBRATION

FIELD

The present disclosure is a non-provisional of and claims priority to U.S. Provisional Patent Application No. 62/516,728 filed on Jun. 8, 2017 and entitled "Devices and Methods of Needle Calibration", which are incorporated herein by reference in their entireties.

FIELD

The present disclosure is generally related to puncture devices, and more particularly to devices and methods of calibrating a puncture needle to achieve a desired insertion depth, such as for lumbar puncture procedures or other needle insertion procedures.

BACKGROUND

Needles may be used in a variety of medical procedures, some of which may require careful attention to the depth to which the needle may be inserted into the patient. For example, infants with fever or signs of a serious bacterial infection routinely undergo a full sepsis evaluation, including a lumbar puncture (LP) procedure. The LP procedure involves a technique for collecting cerebrospinal fluid (CSF) from a patient, and is commonly to identify meningitis in young infants. Such procedures can be difficult, even for experienced physicians and particularly on infants 90 days of age and younger. Unsuccessful LP procedures may be defined by the collection of bloody CFS (such as by puncturing a subdural vessel by advancing the needle too far) or by the failure to collect any fluid.

There are two techniques that have been described that include performing LP procedures in conjunction with sonography (ultrasound). In one technique, the LP procedure involves monitoring the progress of the needle with the aid of ultrasound as the needle is advanced into the spinal canal. This technique may require significant training, dexterity, multiple providers, and a sterile environment. In another technique, the sonography is performed just prior to the LP procedure, and the important landmarks are identified and the patient's skin is marked to assist the provider/operator with the LP procedure.

SUMMARY

In some embodiments, a method may include utilizing sonography to determine a safe depth of needle insertion. The method may further include calibrating a needle to the safe depth. In a particular example, the needle may be inserted into the patient to the safe depth without risk of puncturing the subdural vessels by advancing the needle too far into the patient.

In other embodiments, a device may include a cylindrical body defining an enclosure and including measurement units printed along at least one side. The cylindrical body may include an open end. The device may further include a slidable element configured to close the open end of the cylindrical body. The slidable element may be configured to allow a needle to advance in a first direction into the enclosure and may be configured to attach to the needle when the needle is withdrawn from the enclosure. The slidable may define a stop point for the needle when it is inserted through the skin of a patient.

In still other embodiments, a device may include a tube having substantially cylindrical body defining an enclosure and having an open end. The tube may include measurement units printed along at least one side. The device may further include a slidable element releasably coupled to the open end of the cylindrical body and configured to selectively engage a needle to mark a length of the needle.

In yet other embodiments, a method may include determining a safe depth for insertion of a needle, such an LP needle for extraction of CSF. The method may further include advancing the needle through a slidable element into a tube having measurement units printed on at least one side to a depth corresponding to the safe depth. Additionally, the method can include withdrawing the LP needle from the tube with the slidable element attached at a location configured to limit insertion of the LP needle to a depth that is equal to or less than the safe depth.

In still other embodiments, a needle may include a plurality of markings corresponding to length measurements and weight ranges. In one possible aspect, the markings may provide safe depth indicators for a lumbar puncture procedure based on a determined depth or safe depth ranges for the lumbar puncture procedure based on a weight of the patient.

In another embodiment, a method may include determining a safe depth parameter for insertion of a needle and determining a location on a needle based on measurement units printed on at least one of the needle and a side of a calibration device. The location may correspond to the safe depth parameter. The method may further include marking the needle at the location corresponding to the safe depth parameter.

In still another embodiment, a calibration device may include a housing, an opening extending into the housing and sized to receive a needle, and calibration marks adjacent to the opening. The calibration marks may be configured to define a plurality of weight ranges and to define regularly spaced measurement units. The calibration device may further include an element configured to secure the needle to allow marking of the needle to a selected length based on the calibration marks.

BRIEF DESCRIPTION OF THE DRAWINGS

FIGS. 2A-2B depict perspective views of the device for needle calibration, in accordance with certain embodiments of the present disclosure.

In the following discussion, the same reference numbers are used in the various embodiments to indicate the same or similar elements. Further, it should be appreciated that the drawings are provided for illustrative purposes, and are not necessarily drawn to scale.

DETAILED DESCRIPTION OF ILLUSTRATIVE EMBODIMENTS

Embodiments of a device and methods are described below that may include a depth measuring device that can be used to mark a stop point on a needle, so that the provider, such as a nurse or physician, does not overshoot a selected depth. In a particular embodiment, the device may include a transparent housing including an opening to receive the needle and including a graduated scale or marking lines printed on the side that can be used to measure the needle. In some embodiments, the user may mark the needle according to the measurement, such as by scratching, notching, or drawing on the needle at the measurement location. In some embodiments, the device may include a slidable element configured to attach to the needle to mark a location on the needle. In operation, the mark or the slidable element may provide a depth indicator so that the provider can advance the needle to the selected depth, stopping when the mark or slidable element contacts the surface of the skin. One possible embodiment of a device is described below with respect to FIG. 1 that can be used to provide a depth indicator to assist the provider.

Figure 1:
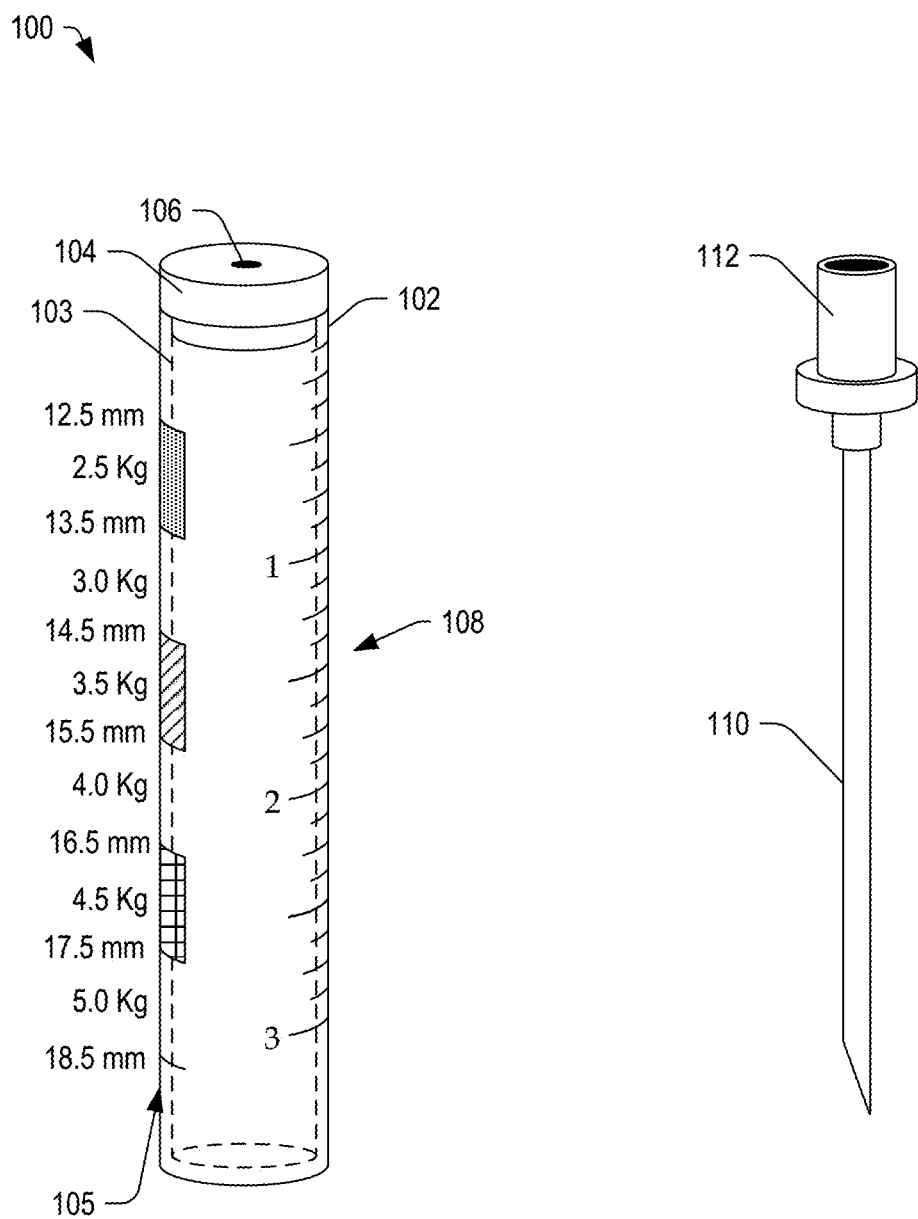
FIG. 1 depicts a perspective view of a device for needle calibration, in accordance with certain embodiments of the present disclosure.

FIG. 1 depicts a perspective view of a device 100 for needle calibration, in accordance with certain embodiments of the present disclosure. The device 100 may include a tube 102 having an open end and having an interior wall 103 indicated by dashed lines. The open end of the tube 102 may include a slidable element 104 with an opening 106 for receiving a needle 110, which may include a connector 112 configured to engage a syringe (not shown). The slidable element 104 may include a first portion that may partially fit within the interior wall 103 of the tube 102 and a second portion that may rest against an end of the tube 102. In the illustrated example, the tube 102 may include a ruler or line gauge 108 that may provide markings at regular intervals that can used to measure the length of the needle 110 to a particular depth, which depth may be indicated by the slidable element 104 when the needle 110 is removed from the tube 102.

In some embodiments, in lieu of or in addition to the ruler or line gauge 108, the tube 102 may include a plurality of regularly spaced markings 105 indicating a length or depth in ten millimeter intervals and optionally indicating a weight range corresponding to a particular depth or range of depths. In some embodiments, the needle depth of distance may be determined as a function of the weight of a patient, according to the following equation:

$$\text{Distance} = 1.7 \times (\text{weight in Kg}) + 8.4 \text{ mm} \quad (1)$$

In Equation (1) above, the weight of the patient can be used to determine the depth to which a needle may be safely inserted in to the patient. Equation (1) was derived from measurements captured of a number of patients over a period of time and based on the observation that the safe depth for each patient is defined by a range. Accordingly, a safe needle depth can be determined based on the weight of the patient, and the needle can be calibrated using the device.

In certain embodiments, a provider may utilize ultrasound or another means to determine a "safe depth" or "maximum safe depth" to which to limit needle advancement. In an LP procedure, for example, the needle may be marked to provide a depth sufficient to extract the CSF without puncturing a subdural vessel, thereby avoiding a bloody LP outcome. In an example, to determine a safe depth, a physician or other provider may utilize an ultrasound machine to determine measurements from a patient.

In a particular embodiment, an ultrasound machine may be used on a patient to determine a needle insertion depth that is safe for the patient and that will be effective for the particular procedure. In the following discussion, for ease of reference, the needle puncture depth measurements and the associated devices are described with respect to a LP procedure. However, it should be understood that the devices and methods may also be applied to other medical procedures for which the depth of needle insertion is of concern.

In a particular example involving a LP procedure, a patient may be positioned in the lateral decubitus flexed position (right or left), and a 10-MHz linear array probe may be used in the longitudinal midline orientation to identify the conus medullaris, the L1 through L5 lumbar vertebrae, and the corresponding dural space. The interspace below the conus with the greatest amount of cerebral spinal fluid (typically L3 to L5) may be selected, centered on the ultrasound machine screen, and marked with a skin pen immediately next to the center of the ultrasound probe. The probe may then be rotated ninety degrees to identify the same space in the transverse view, and another mark with the skin pen may be made. The marks may be extended at a 90 degree angle to one another to create a cross over the lumbar interspace of interest, marking the site of the lumbar puncture.

In some embodiments, with probe in the longitudinal orientation, the provider may identify the conus as an anechoic structure that tapers and turns into an echogenic filum terminale approximately at the level of the T12 to L1 vertebra. In general, the filum continues caudally and is surrounded by the echogenic fibers of the cauda equine and hypoechoic cerebral spinal fluid. The provider may use the ultrasound to determine the distance from the skin to the anterior dural border through the interspace of interest at a 90 degree angle. This measurement represents the "safe depth" to which the needle 110 may be advanced in order to extract CSF without inadvertently puncturing a subdural blood vessel.

The provider may utilize the measurement data to mark the needle 110 at a length that corresponds to the "safe depth", which may be equal to or slightly less than the "safe depth" (for example, between a sixteenth of an inch of a "maximum safe depth").

FIGS. 2A-2B depict perspective views of the device for needle calibration, in accordance with certain embodiments of the present disclosure. In FIG. 2A, the provider may advance a needle 110 through the slidable element 104 to a depth corresponding to the "safe depth" as determined from the ruler or line gauge 108 printed on the side of the tube 102. Once the end of the end of the needle 110 reaches a selected depth corresponding to the line gauge 108 or the regularly spaced markings 105, the provider may withdraw the needle 110 from the tube 102, and the slidable element 104 may adhere to the needle 110 and may be withdrawn as the needle 110 is withdrawn, marking the selected depth.

As depicted in FIG. 2B, a marked needle 210 may include the slidable element 104 indicating or marking a stopping point for the provider. In particular, the slidable element 104 may form a marker of the "safe depth", providing a visible indicator that may be used by the provider to advance the needle 110 to the appropriate depth for extraction of the cerebral spinal fluid from the patient. In a particular example, the provider may safely advance the needle 110 into the patient until the slidable element 104 contacts the patient's skin.

It should be understood that the embodiment depicted in FIG. 1 represents one possible embodiment, and that other embodiments are also possible. Further, it should be understood that the illustrated example is not necessarily drawn to scale. Additionally, it should be appreciated that the "safe depth" may vary from patient to patient, depending on certain variables, such as the patient's age, height, weight, body type, and so on. Other embodiments are also possible.

Figure 3:
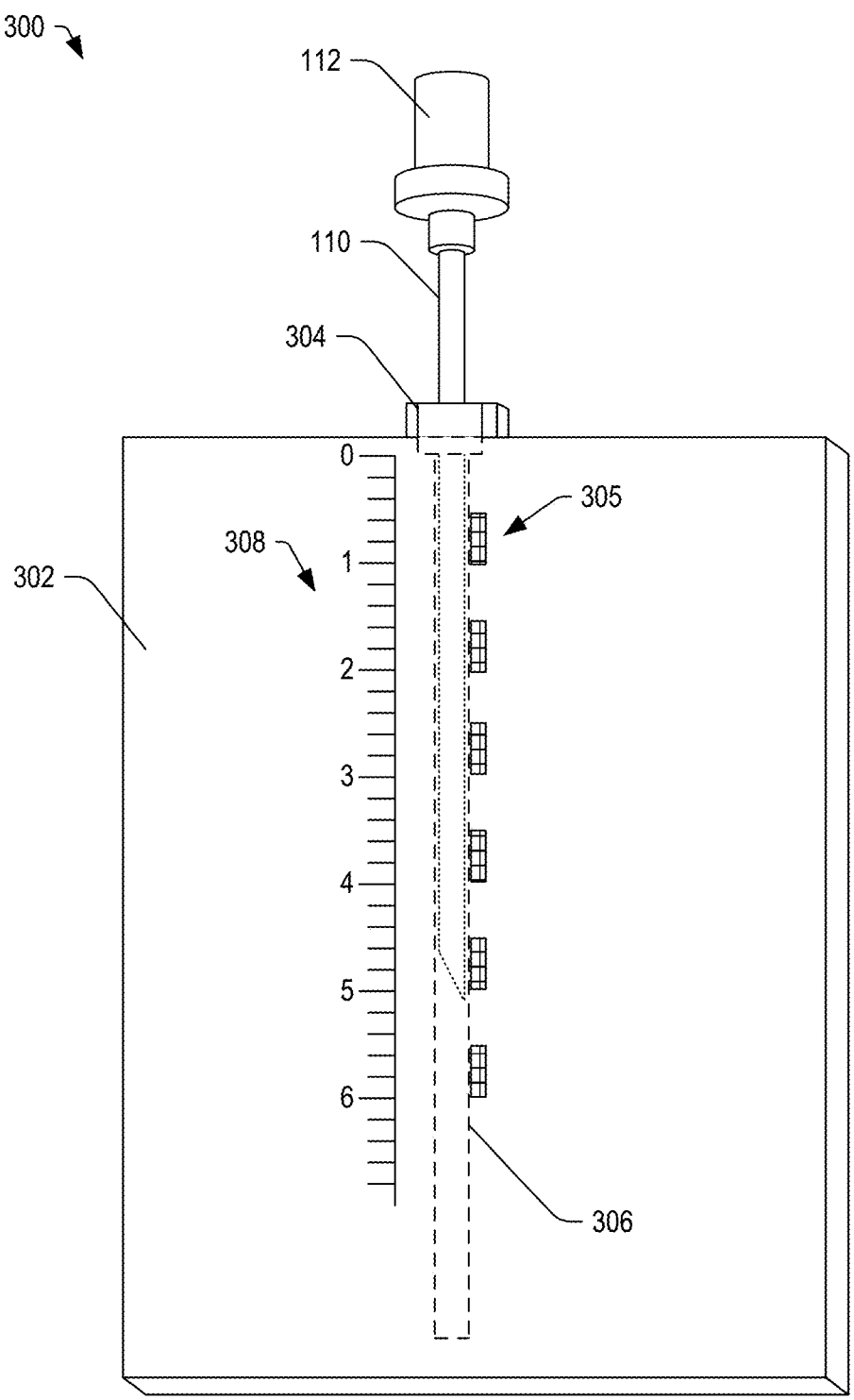
FIG. 3 depicts a device for needle calibration, in accordance with certain embodiments of the present disclosure.

FIG. 3 depicts a device 300 for puncture needle calibration, in accordance with certain embodiments of the present disclosure. The device 300 may include a housing 302 including a channel 306 configured to receive the needle 110. Measurement marks 308 or other regular spaced markings 305 (defining lengths and optionally weight ranges) may be printed on the surface of the housing 302 adjacent to the channel 306. The housing 302 may be formed from a substantially transparent material (at least one a side corresponding to the measurement marks 308), allowing a user to measure the length of the needle 110 from the measurement marks 308 or spaced markings 305. The device 300 can also include a slidable element 304 configured to fit over the channel 306 and to receive the needle 110. In the illustrated example, the slidable element 304 may have an irregular shape or may have one or more flat sides.

In certain embodiments, the needle 110 may be advanced through the slidable element 304 and into the channel 306 to a selected depth (as determined by comparing the end of the needle 110 to the measurement marks 308 or spaced markings 305). Once the needle 110 is measured to the desired depth, the needle 110 may be withdrawn, causing the slidable element 304 to be removed from the housing 302 at a location on the needle 110 marking the selected depth as described above with respect to FIG. 2B.

In the illustrated example, the device 300 is shown as having a substantially rectangular prism shape. However, the device 300 is not limited to cylindrical shapes (FIGS. 1-2B) or rectangular shapes (FIG. 3). Rather, the device 300 may have any shape provided that the device can receive the needle 110. Other embodiments are also possible.

In the above-described embodiments, a slidable element may be configured to adhere to the needle to mark a safe depth. However, in other embodiments, the slidable element may be configured to secure the needle 110 within the devices to secure the needle 110 to allow a provider to mark the needle 110. The provider may mark the needle 110 using a marker, a pen, a scratch, a piece of tape, another indicator, or any combination thereof.

Figure 4A:
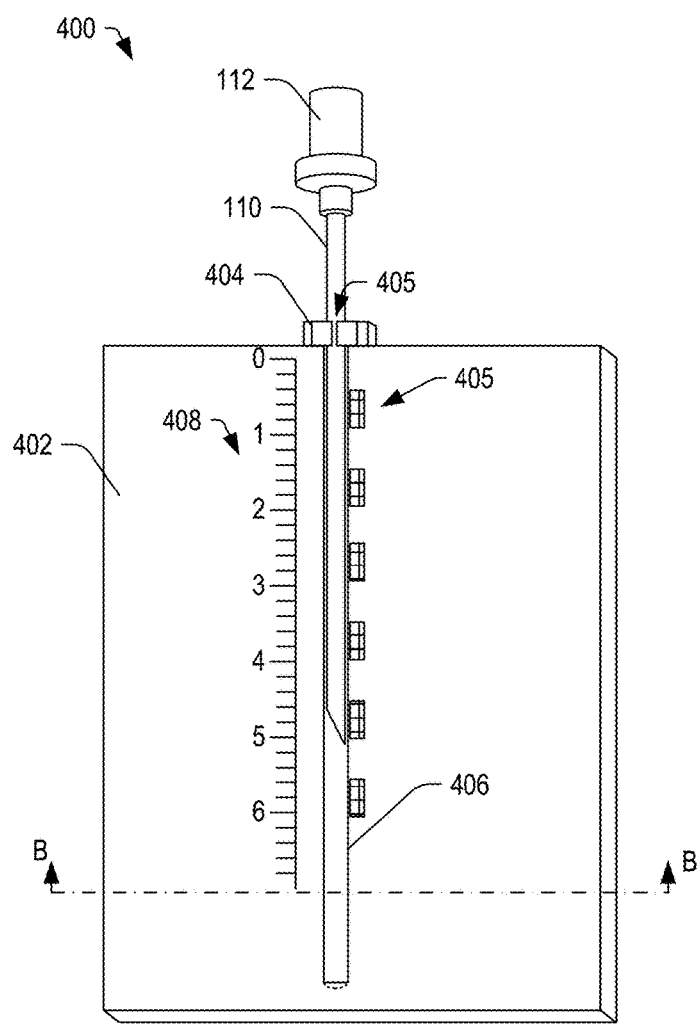
FIG. 4A depicts a device for needle calibration including a slot sized to engage a needle, in accordance with certain embodiments of the present disclosure.

FIG. 4A depicts a system 400 including a device 402 for needle calibration including a slot 406 sized to engage a needle 110, in accordance with certain embodiments of the present disclosure. The slot 406 may be a depression or groove carved into the external surface of the device 402. The device 402 may further include measurement marks 408 or regular spaced marks 405 (indicating lengths and optionally weight ranges) printed on a surface of the device 402 next to the slot 406.

In some embodiments, a clipping element 404 may include an opening 405 through which the needle 110 may be pressed. The clipping element 404 may receive the needle 110 through the opening 405 to secure the needle 110 and to hold the needle 110 within the slot 406. In some embodiments, the needle 110 may be positioned within the slot 406 at a desired measurement length and pressed into the clipping element 404 to hold the needle 110 for marking. In some examples, the clipping element 404 may be slidable and removable, making it possible to use the clipping element 404 as the mark on the needle 110 to indicate a safe depth. Other embodiments are also possible.

Figure 4B:
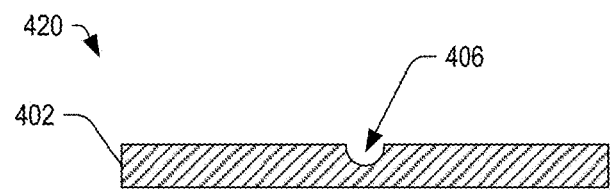
FIG. 4B depicts a cross-sectional view of the device of FIG. 4A taken along line B-B in FIG. 4A.

FIG. 4B depicts a cross-sectional view 420 of the device 402 of FIG. 4A taken along line B-B in FIG. 4A. The device 402 may include the slot 406, which may be etched into the surface of the device 402. The needle 110 may be positioned in the slot 406 and secured by the clipping element 404 to allow a provider to mark the needle 110.

Figure 5A:
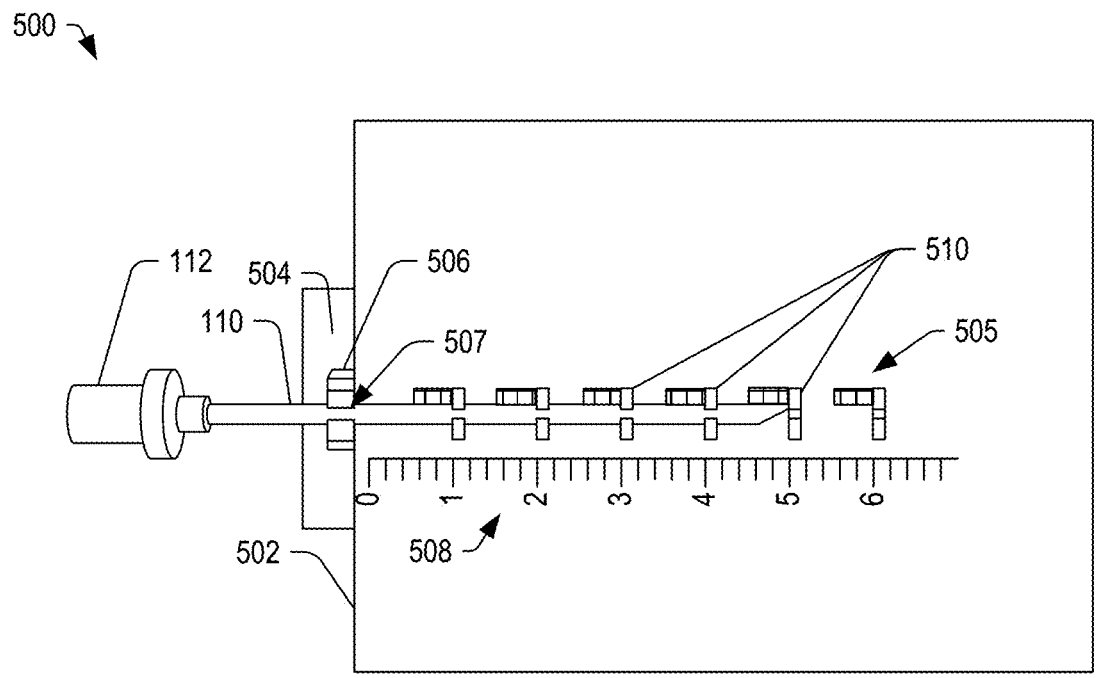
FIG. 5A depicts a device for needle calibration including a plurality of holding clips, in accordance with certain embodiments of the present disclosure.

FIG. 5A depicts a system 500 including a device 502 for needle calibration including a plurality of holding clips 506 and 510, in accordance with certain embodiments of the present disclosure. The clip 506 may be coupled to an extension 504 that may extend from the device 502. The system 500 may include a needle 110, which can be placed into the clip 506 and compared against the measurement marks 508 or spaced markings 505 (indicating a length and/or a weight range). The clips 506 and 510 may cooperate to hold the needle 110 to allow a provider to mark the needle 110. Other embodiments are also possible.

In some embodiments, the clips 506 and 510 may be substantially v-shaped clips sized to receive and secure the needle 110. In some embodiments, the clip 506 may be removable and can remain coupled to the needle 110 to mark a safe depth. When the clip 506 is used as the marker, the cutout portion 507 may facilitate viewing of the needle insertion site at the skin level. In other embodiments, the provider may mark the needle 110 to the calibrated length according to any of the above-described marking techniques.

Figure 5B:
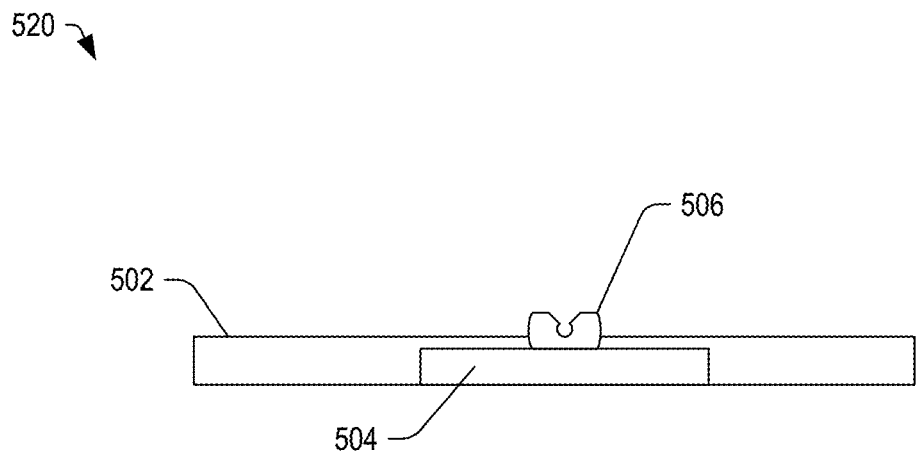
FIG. 5B depicts a side view of the device of FIG. 5B.

FIG. 5B depicts a side view 520 of the device 502 of FIG. 5B. The side view 520 includes the substantially v-shaped clip 506 can receive and releasably secure the needle 110 to facilitate marking of the safe depth. Other embodiments are also possible.

Figure 6A:
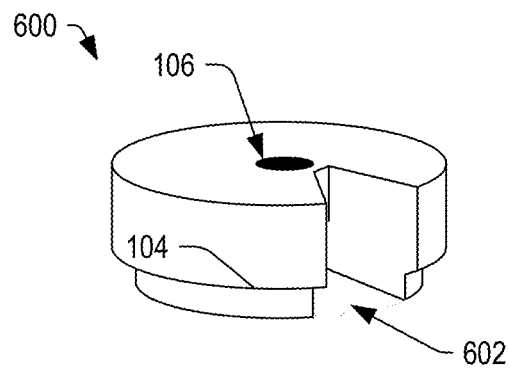
FIGS. 6A, 6B, and 6C depict embodiments of a slidable element including a V-shaped cut to facilitate viewing of the insertion site, in accordance with certain embodiments of the present disclosure.
Figure 6B:
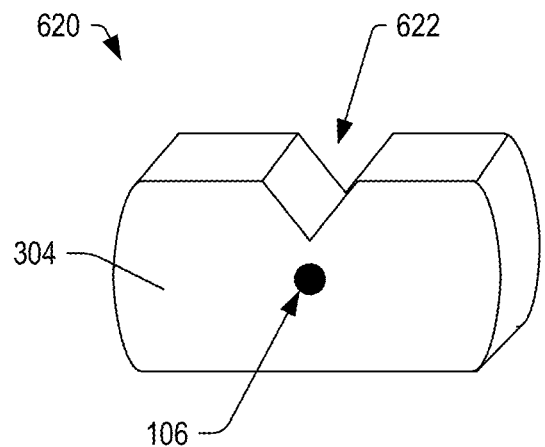

FIGS. 6A and 6B depict embodiments of a slidable element including a V-shaped cut to facilitate viewing of the insertion site, in accordance with certain embodiments of the present disclosure. In FIG. 6A, an embodiment 600 of the slidable element 104 of FIG. 1 is shown, which may include a cutout 602 which extends from a peripheral edge toward (but not all the way into) the opening 106. The cutout 602 may have a substantially v-shaped profile, which may facilitate viewing of the needle insertion site at the skin level. The cutout 602 may allow the provider to view the insertion site without having to lean over the needle 110 to see the needle insertion.

In FIG. 6B, an embodiment 620 of the slidable element 304 of FIG. 3 is shown, which may include a cutout 622 that extends from a side toward (but not all the way into) the opening 106. The cutout 622 may facilitate viewing of the needle insertion site at the skin level. Other embodiments are also possible.

Figure 6C:
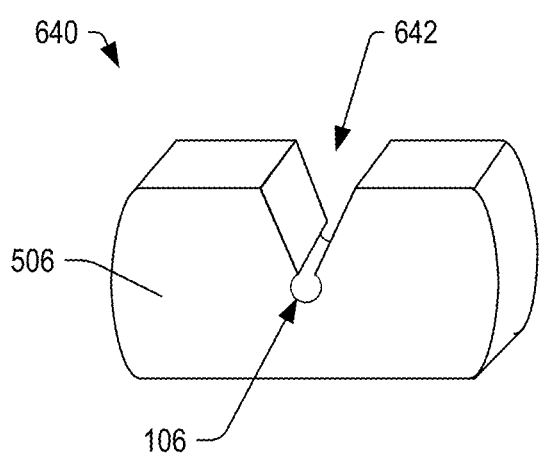

In FIG. 6C, an embodiment 640 of the clip 506 of FIG. 5 may include a cutout 642 that extends into a substantially cylindrical opening 106. The cutout 642 and opening 106 may cooperate to receive and secure a needle 110, as discussed with respect to FIGS. 5A and 5B. In the embodiment 640, the cutout 642 may provide a dual purpose including facilitating reception of the needle 110 and facilitating viewing of the needle insertion site at the skin level. Other embodiments are also possible.

Figure 7:
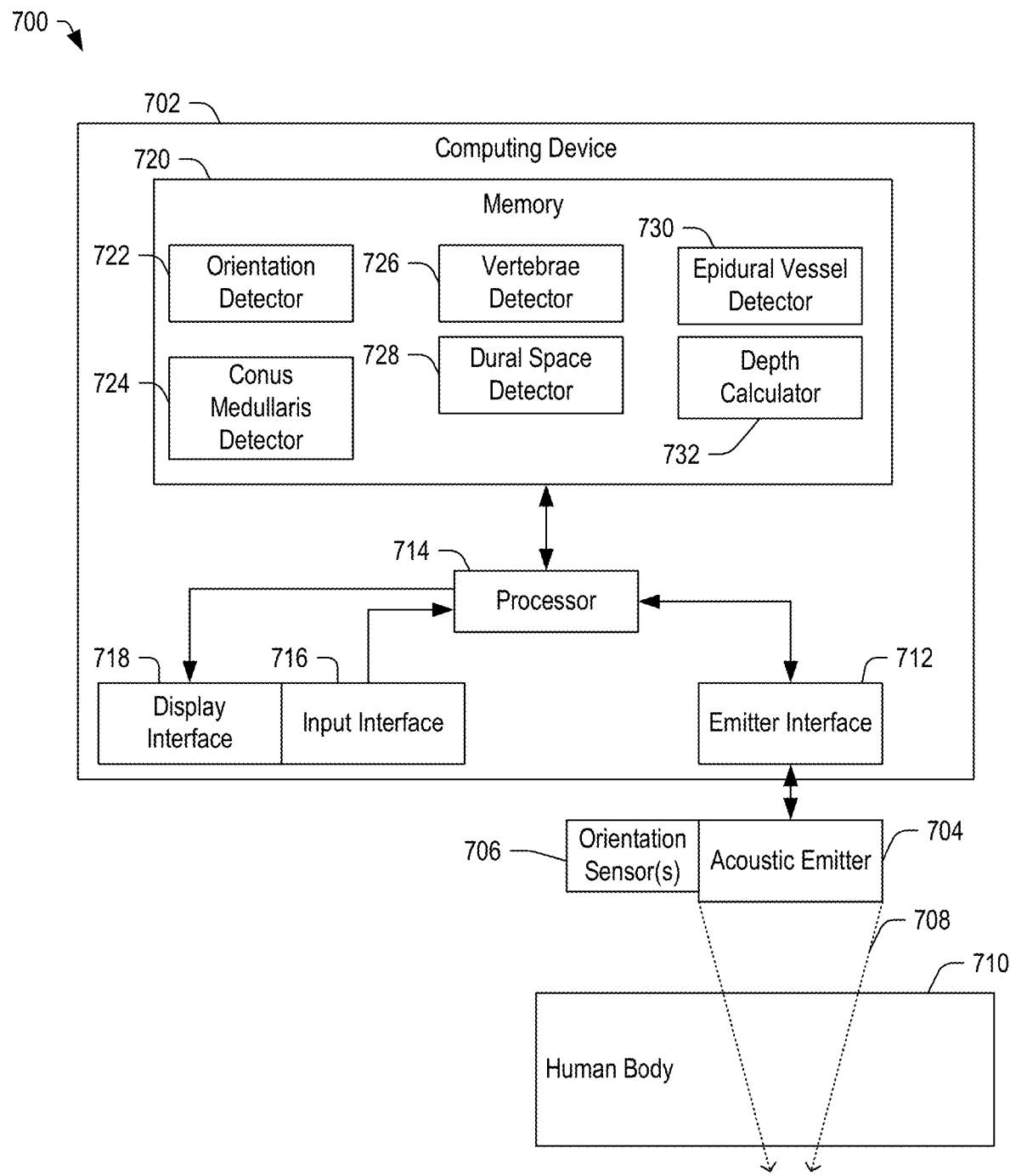
FIG. 7 depicts a system that can be used in conjunction with a needle calibration device, in accordance with certain embodiments of the present disclosure.

FIG. 7 depicts a system 700 that can be used in conjunction with the needle calibration devices of FIGS. 1-3, in accordance with certain embodiments of the present disclosure. The system 700 may include a computing device 702 coupled to an acoustic emitter 704 and optionally one or more orientation sensors 706. In an example, the system 700 can include an ultrasound machine. The system 700 may cooperate with the acoustic emitter 704 to direct ultrasonic signals 708 toward and into a human body, generally indicated at 710, and to receive reflected signals, which may be converted into electrical signals that may be interpreted by the computing device 702.

The computing device 702 may include an emitter interface 712 coupled to the acoustic emitter 704 and the one or more orientation sensors 706. The emitter interface 712 may be coupled to a processor 714. The processor 714 may also be coupled to an input interface 716 and a display interface 718. In some embodiments, the input interface 716 and the display interface 718 may be combined in the form of a touchscreen. In other embodiment, the input interface 716 may include or may be coupled to a keypad or keyboard, a stylus, a mouse, or other input device to receive data. The display interface 718 may include or may be coupled to a display.

The computing device 702 may also include a memory 720 coupled to the processor 714. The memory 720 may store data as well as instructions that may be executed by the processor 714. In some embodiments, the memory 720 may include an orientation detector 722 that, when executed, may cause the processor 714 to determine an orientation of the acoustic emitter 704 relative to the body of the patient based on data derived from the one or more orientation sensors 706. The memory 720 may further include a conus medullaris detector 724 that, when executed, may cause the processor 714 to determine the conus medullaris of the patient based on the ultrasonic data. In some embodiments, the memory 720 may also include a vertebrae detector 726 that, when executed, may cause the processor 714 to analyze data received from the acoustic emitter 704 to detect one or more vertebrae and to automatically identify the vertebrae.

The memory 720 may further include a dural space detector 728 that, when executed, may cause the processor 714 to automatically detect the anatomic space that is the outermost part of the spinal canal based on the data from the acoustic emitter 704. The memory 720 may also include an epidural vessel detector 730 that, when executed, may cause the processor 714 to analyze the data from the acoustic emitter 704 to determine epidural blood vessels. In some embodiments, the memory 720 may include a depth calculator 732 that, when executed, may cause the processor 714 to determine a "safe depth" for needle insertion to avoid puncturing a blood vessel.

In some embodiments, the system 700 may represent a least a portion of an ultrasound machine. A provider may utilize the system 700 to determine a suitable depth for needle insertion. Subsequently, the provider may utilize the device 100 of FIGS. 1-2B to mark a needle 110 at a location corresponding to the determined depth.

Figure 8:
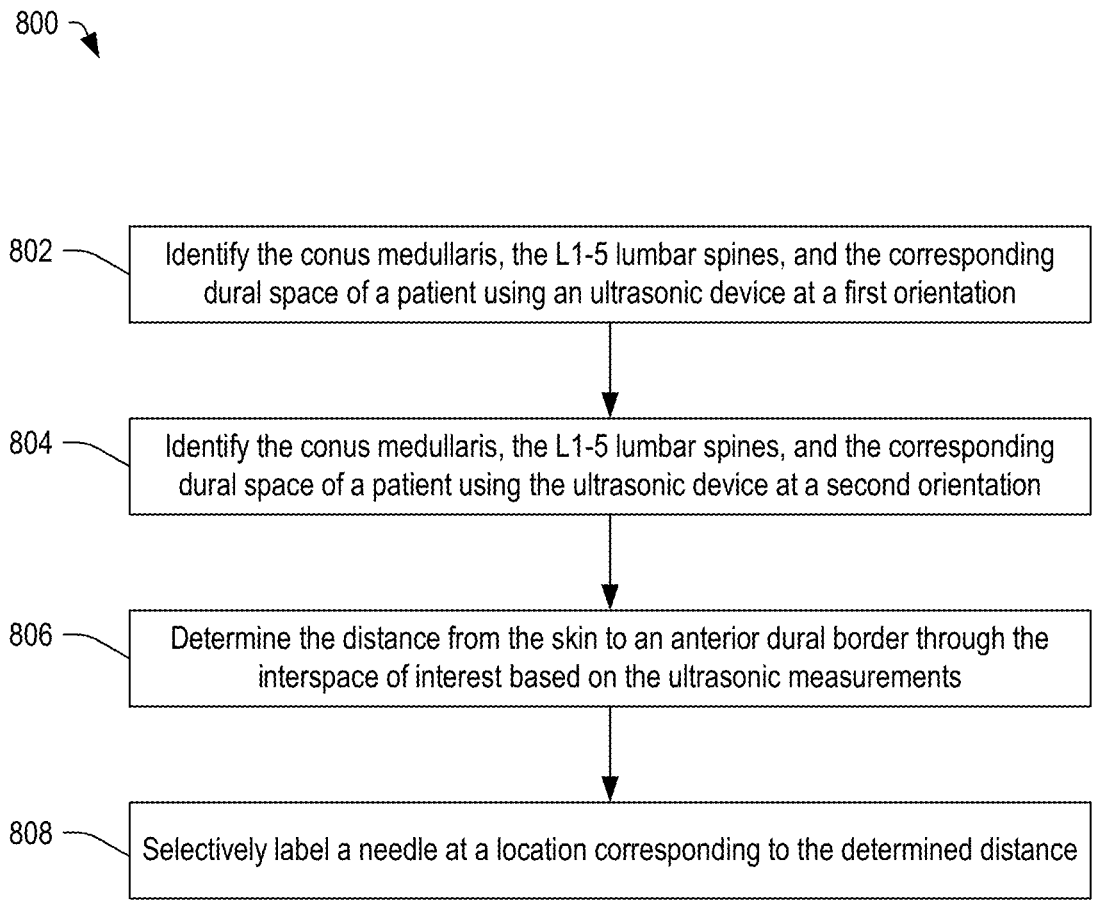
FIG. 8 illustrates a method of labeling a needle based on ultrasonic measurements, in accordance with certain embodiments of the present disclosure.

FIG. 8 illustrates a method 800 of labeling a needle based on ultrasonic measurements, in accordance with certain embodiments of the present disclosure. At 802, the method 800 may include identifying the conus medullaris, the L1-5 Lumbar spines, and the corresponding dural space of a patient using an ultrasonic device at a first orientation. At 804, the method 800 can include identifying the conus medullaris, the L1-5 Lumbar spines, and the corresponding dural space of a patient using an ultrasonic device at a second orientation. In some embodiments, the first orientation may be longitudinal to the patient's back, while the second orientation may be transverse to the patient's back (i.e., from the side).

At 806, the method 800 can include determining a distance from the skin to an anterior dural border through the interspace of interest based on the ultrasonic measurements. In some embodiments, the measurements may be taken during the identifying operations of 802 and 804.

At 808, the method 800 can include selectively labeling a needle at a location corresponding to the determined distance. As discussed above, the provider may utilize the device of FIGS. 1-3 to mark the needle 110 at a certain depth. In a particular example, the slidable element may slide along the needle to mark the needle at the determined depth. The provider may then insert the needle through the patient's skin to the desired depth in order to withdraw cerebral spinal fluid.

Figure 9:
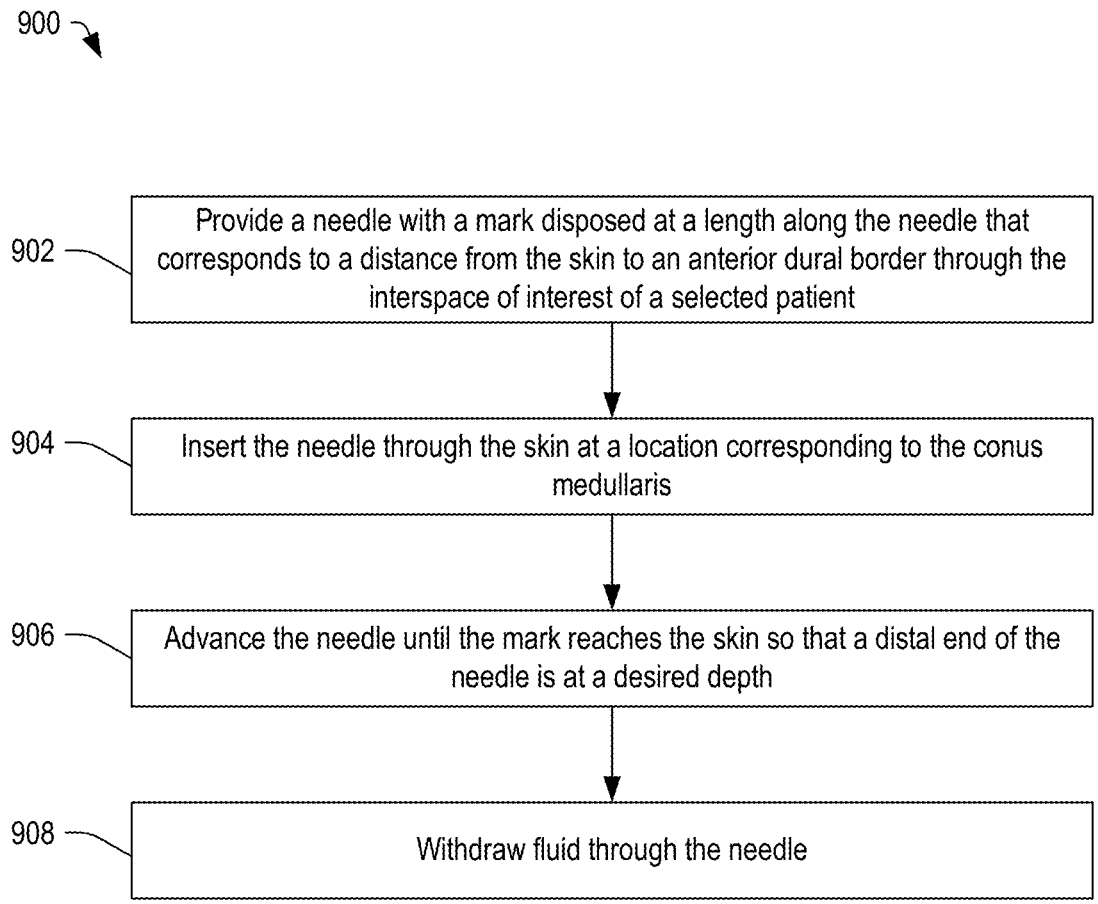
FIG. 9 illustrates a method of utilizing a needle labeled according to the method of FIG. 8.

FIG. 9 illustrates a method 900 of utilizing a needle labeled according to the method of FIG. 8. At 902, the method 900 may include providing a needle with a mark disposed at a length along the needle that corresponds to a distance from the skin to an anterior dural border through the interspace of interest of a selected patient. The needle may be provided by marking the needle at a particular depth corresponding to a particular patient according to one of the methods described above.

At 904, the method 900 can include inserting the needle through the skin of the patient at a location corresponding to the conus medullaris. In some embodiments, the needle may be inserted at an angle that is approximately ninety degrees relative to the patient's back.

At 906, the method 900 can include advancing the needle until the mark reaches the skin so that the distal end of the needle is at a desired depth. In some embodiments, the mark may include a slidable element coupled to the needle to mark the desired depth. Other embodiments are also possible.

At 908, the method 900 may include withdrawing fluid through the needle. In a particular embodiment, the fluid may include cerebral spinal fluid. Other embodiments are also possible.

Figure 10:
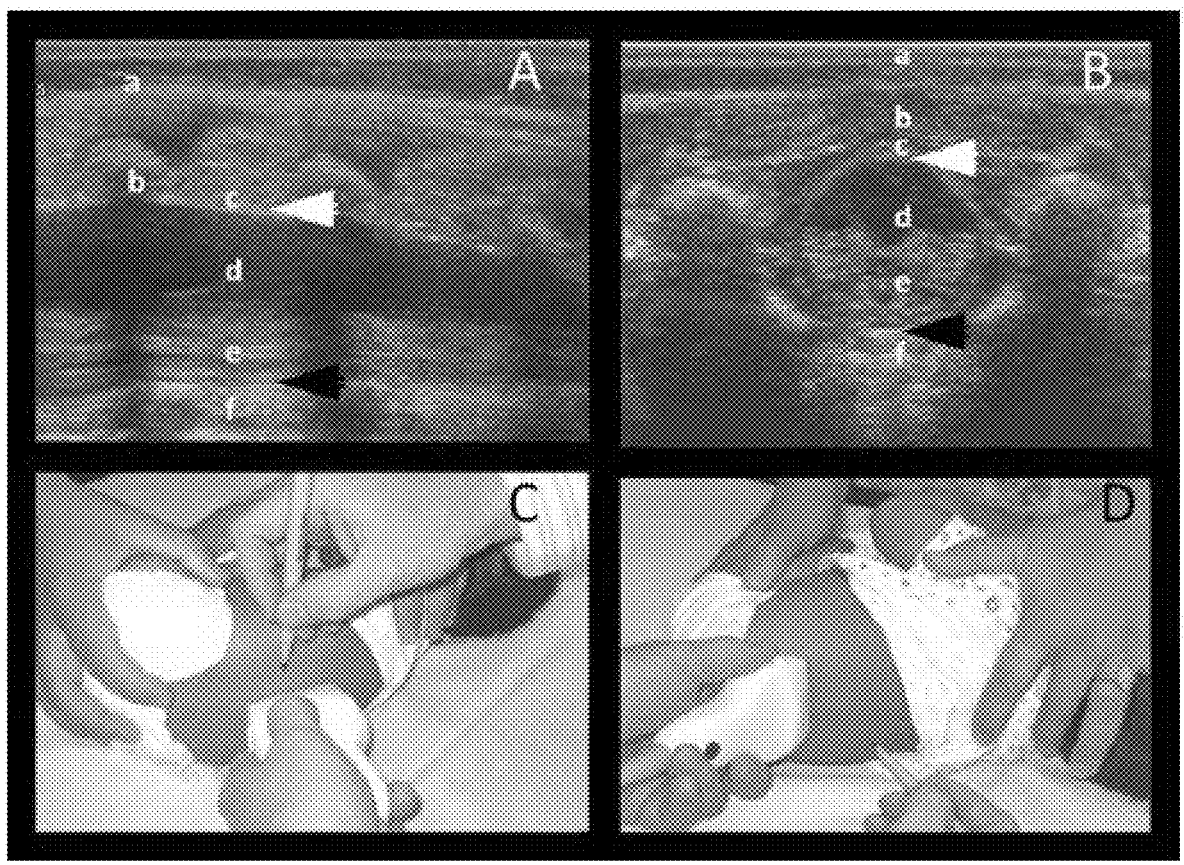
FIG. 10 depicts ultrasonic findings and probe orientations in longitudinal (A and C) and transverse (B and D) view of the lower spine, in accordance with certain embodiments of the present disclosure.

FIG. 10 depicts images 1000 of ultrasonic findings and probe orientations in longitudinal (A and C) and transverse (B and D) views of the lower spine, in accordance with certain embodiments of the present disclosure. The images include elements corresponding to a pre-lumbar puncture evaluation of spinal landmarks. In image C, the provider is using an ultrasonic probe to determine spinal landmarks from the longitudinal view and the provider is applying a mark on the skin of the patient corresponding to the measurement location. In image A, the corresponding ultrasonic view of the patient is shown.

In image D, the provider is using an ultrasonic probe to determine the spinal landmarks from the transverse view. Further, the provider is applying a mark on the skin of the patient corresponding to the measurement location. In image B, the corresponding ultrasonic view of the patient is shown.

In Images A and B, certain landmarks are labeled using lowercase letters. The lowercase letter (a) in the images A and B represents the subcutaneous tissue. Further, the lowercase letter (b) represents the spinus process with bone shadowing. The lowercase letter (c) demarks the epidural space. The lowercase letter (d) represents the cerebral spinal fluid within the dural sac. The lowercase letter (e) depicts the cauda equine nerves. The lowercase letter (f) represents the vertebral body. The posterior dural border is indicated by a white arrow, while the anterior dural border is indicated by a black arrow.

As depicted in FIG. 10, the ultrasonic measurements may be used to determine the needle depth. Once the depth is determined from the measurements, as discussed above, the needle may be marked or labeled to denote the selected depth. Other embodiments are also possible.

In the image A, the interspace below the conus with the greatest amount of cerebral spinal fluid (typically L3 to L5) was selected, centered on the ultrasound machine screen and marked with a skin pen (depicted in image C) immediately next to the center of the ultrasound probe. The probe was then turned ninety degrees to identify the same space in the transverse view and another mark was made (images B and D). The skin pen marks may then be extended at a ninety degree angle to one another to create a cross over the lumbar interspace of interest, marking the site of the lumbar puncture.

Figure 12:
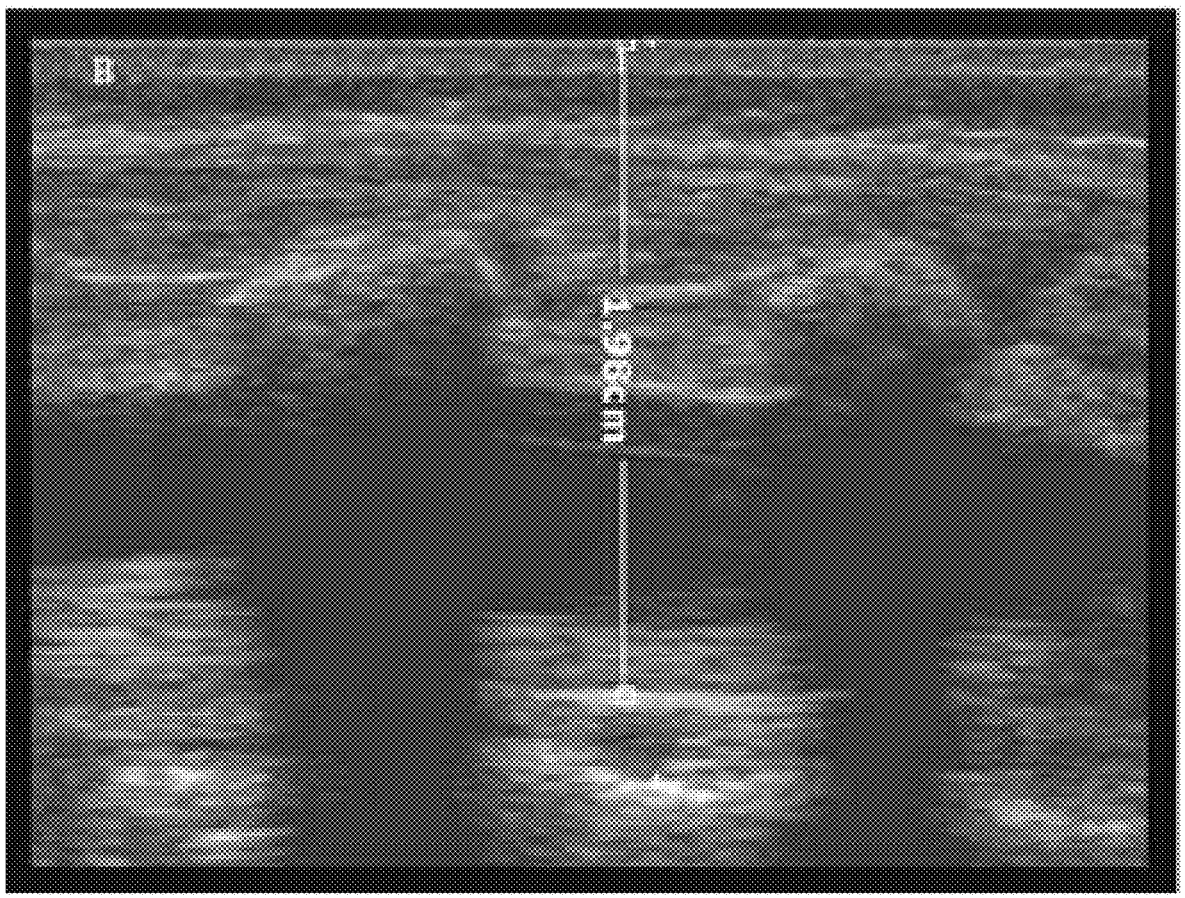
FIG. 12 depicts an image of a measurement of the safe depth taken from the skin to the anterior border of the dural sac at the L3-L4 interspace, in accordance with certain embodiments of the present disclosure.

With the sonographic probe in the longitudinal view of image A, the conus can be identified as an anechoic structure that tapers and turns into an echogenic filum terminale approximately at the level of the T12 through L1 vertebrae. The filum continues caudally and is surrounded by the echogenic fibers of the cauda equine and hypoechoic cerebral spinal fluid. The distance from the skin to the anterior dural border can then be measured through the interspace of interest at a ninety degree angle. This measurement may represent the "safe depth" and can be marked on the spinal needle with calipers and a sterile skin marker (as depicted in FIG. 12). In some embodiments, the measurement may be marked by inserting the needle through the slidable element of the device to the safe depth and then removing the needle, which may retain the slidable element to mark the depth.

The true distance to reach the vasculature in the epidural space will be longer than the sonographic safe depth, since the needle is typically directed cephalad (typically at an angle of 30 to 70 degrees). This depth is explained by the Pythagorean Theorem and demonstrated in FIG. 12.

Figure 11:
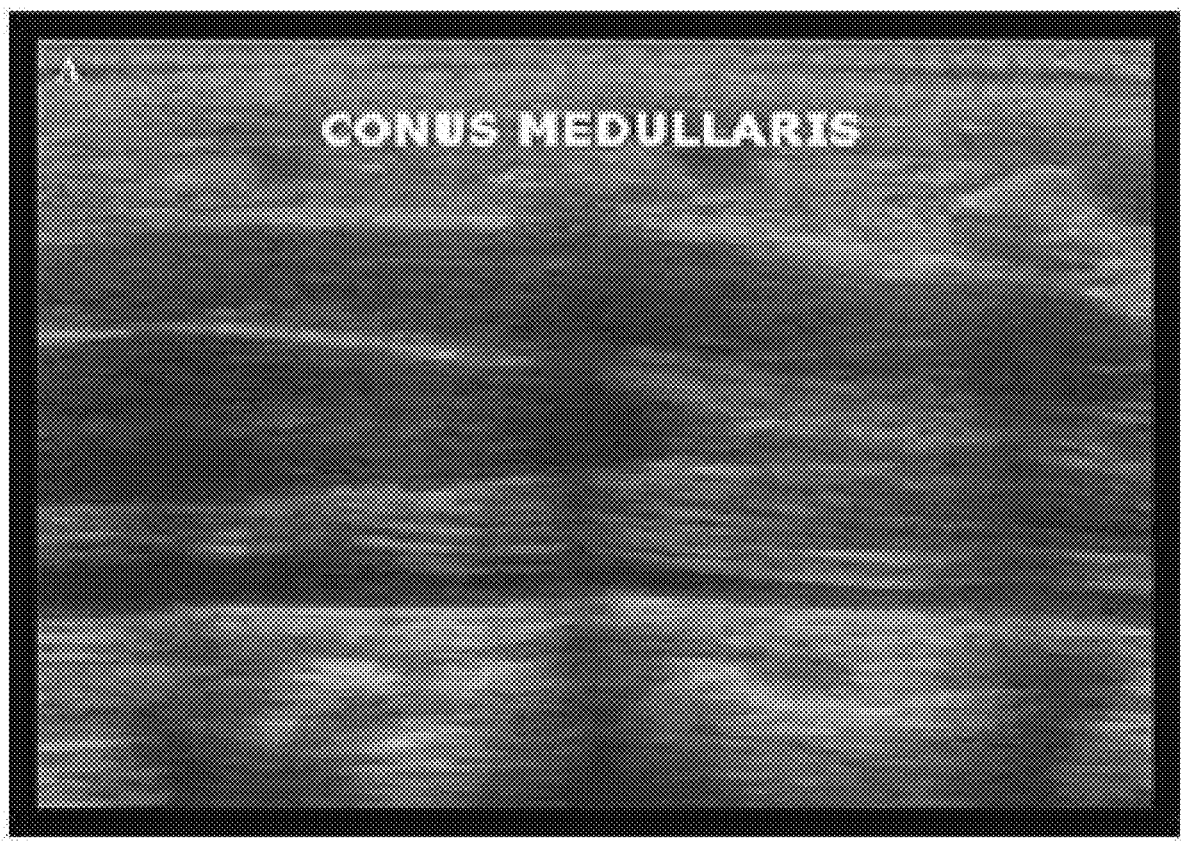
FIG. 11 depicts an ultrasonic image identifying the conus medullaris at the T12-L2 spinal level, in accordance with certain embodiments of the present disclosure.

FIG. 11 depicts an ultrasonic image 1100 identifying the conus medullaris at the T12-L2 spinal level, in accordance with certain embodiments of the present disclosure. In a particular embodiment, the ultrasonic probe can be used to identify the conus medullaris at the T12 to L2 spinal level. The ultrasonic probe may then be advanced caudally to determine measurements of the safe depth as shown in FIG. 12.

FIG. 12 depicts an image 1200 of a measurement of the safe depth taken from the skin to the anterior border of the dural sac at the L3-L4 interspace, in accordance with certain embodiments of the present disclosure. The ultrasonic probe may be advanced caudally, and a measurement of the safe depth is taken from the skin to the anterior border of the dural sac at the L3 to L4 interspace. The depth may be used to measure the length of the needle to correspond to the determined safe depth. An example of the measurement is shown in FIG. 13.

Figure 13:
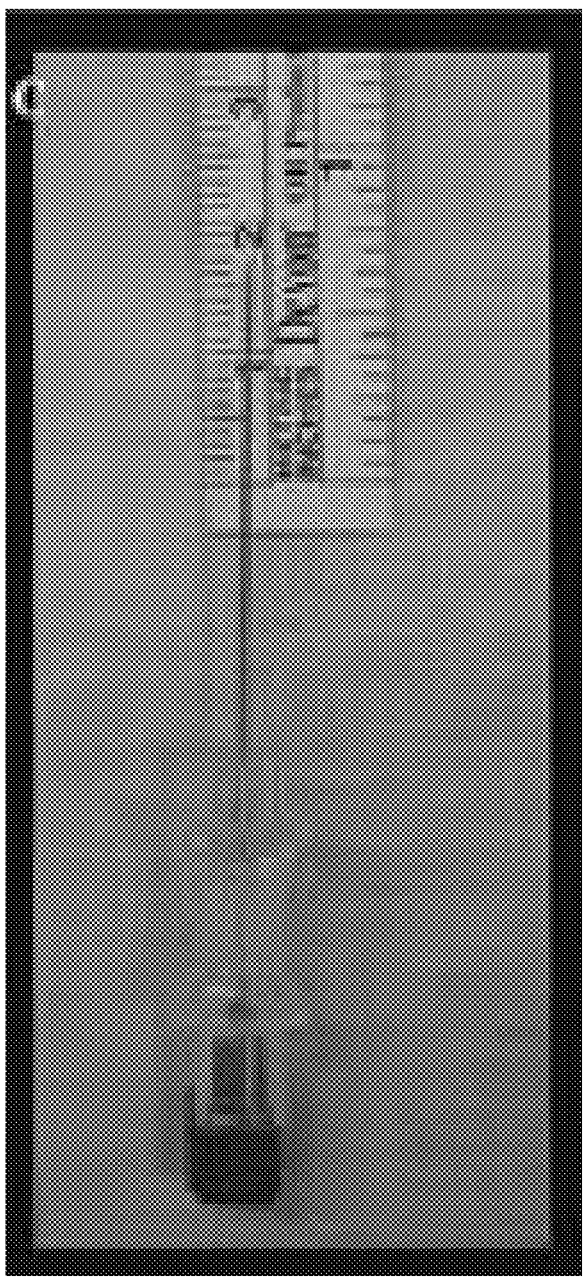
FIG. 13 depicts a spinal needle marked at the safe depth using a caliper, in accordance with certain embodiments of the present disclosure.

FIG. 13 depicts a spinal needle 1300 marked at the safe depth using a caliper, in accordance with certain embodiments of the present disclosure. In the illustrated example, the needle is shown next to a ruler.

Figure 14:
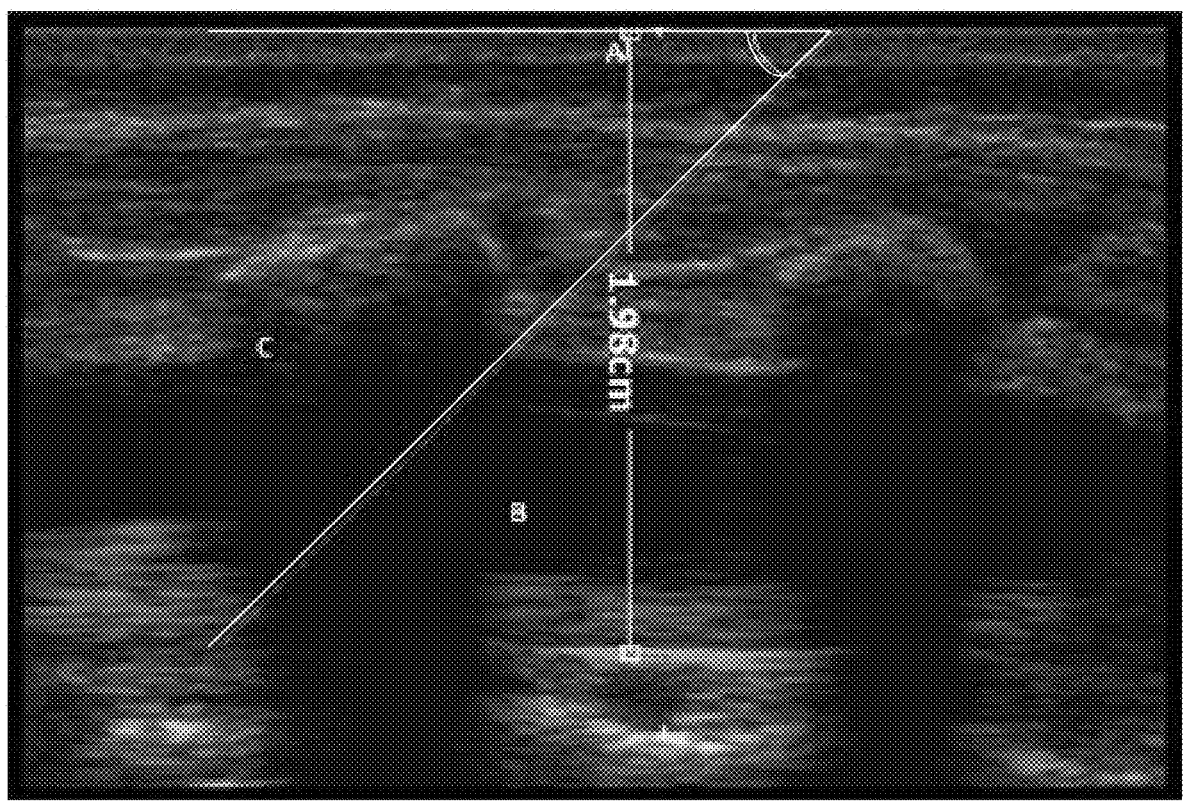
FIG. 14 depicts an image of a measurement of the safe depth taken from the skin to the anterior border of the dural sac at the L3-L4 interspace and depicting a needle insertion angle, in accordance with certain embodiments of the present disclosure.

FIG. 14 depicts an image 1400 of a measurement of the safe depth taken from the skin to the anterior border of the dural sac at the L3-L4 interspace and depicting a needle insertion angle, in accordance with certain embodiments of the present disclosure. As illustrated in FIG. 14, the mathematical theory of the safe distance can make use of the Pythagorean Theorem. In particular, the perpendicular distance from the skin to the anterior dural border and the needle angle can be used to determine the distance from the skin to the anterior dural border at the given angle of entry. A trigonometric equation can be used to compute the safe distance for any given insertion angle.

As discussed above, because the entry angle is typically less than 90 degrees, the safe depth is typically greater than the marked needle length. In particular, during the lumbar puncture procedure, if the needle marking is reached without obtaining cerebral spinal fluid, a provider may understand that there is a small amount of space left to safely advance the needle based on the angle of entry. The provider's option is to proceed with caution, redirect and/or withdraw the needle, or attempt the procedure again.

Figure 15:
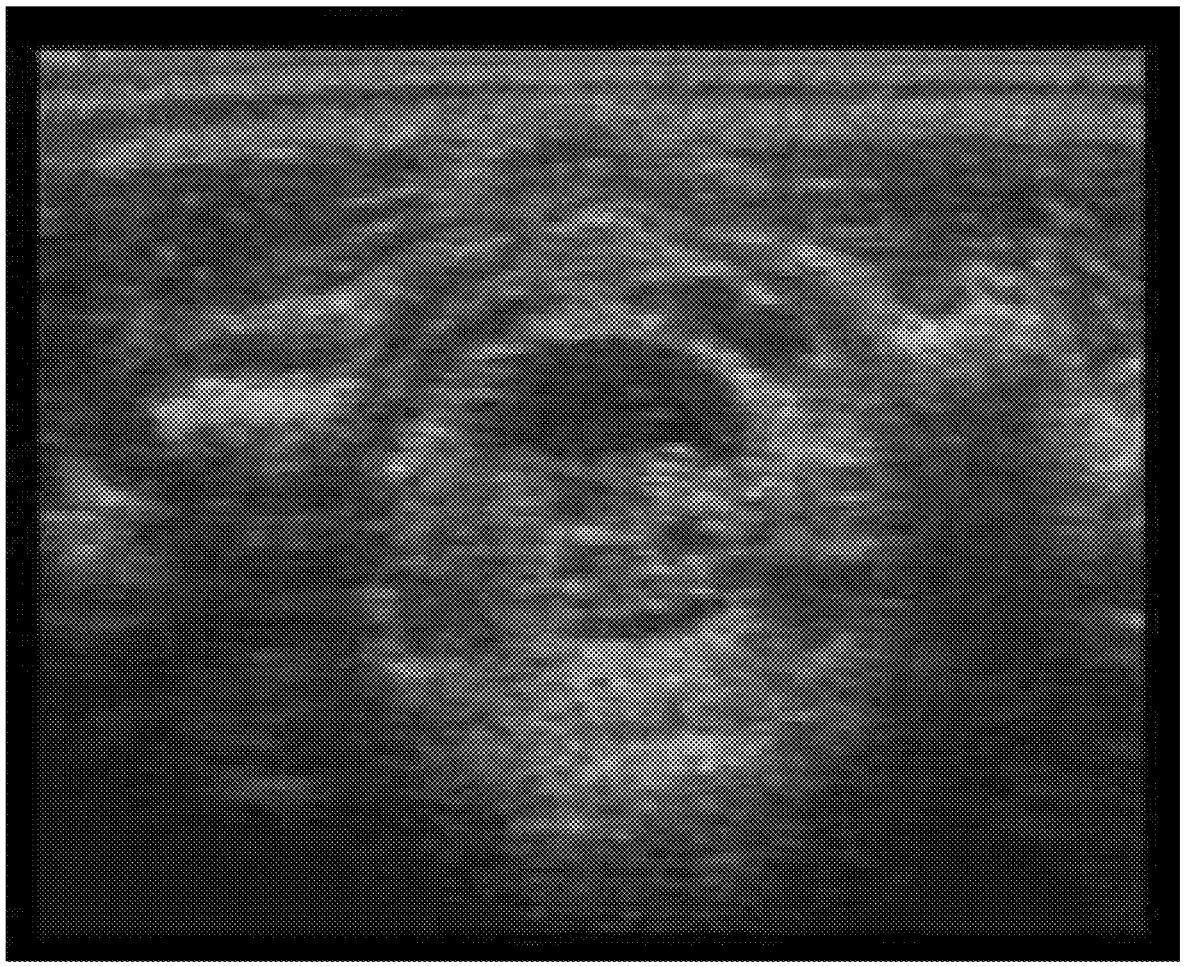
FIG. 15 depicts a transverse view of the spinal canal and depicting epidural vessels.

FIG. 15 depicts a transverse view of the spinal canal 1500 and depicting epidural vessels. The epidural vessels are visible about the periphery of the spinal column. The location of the epidural vessels may be determined so that the provider can avoid puncturing the epidural vessels.

Figure 16:
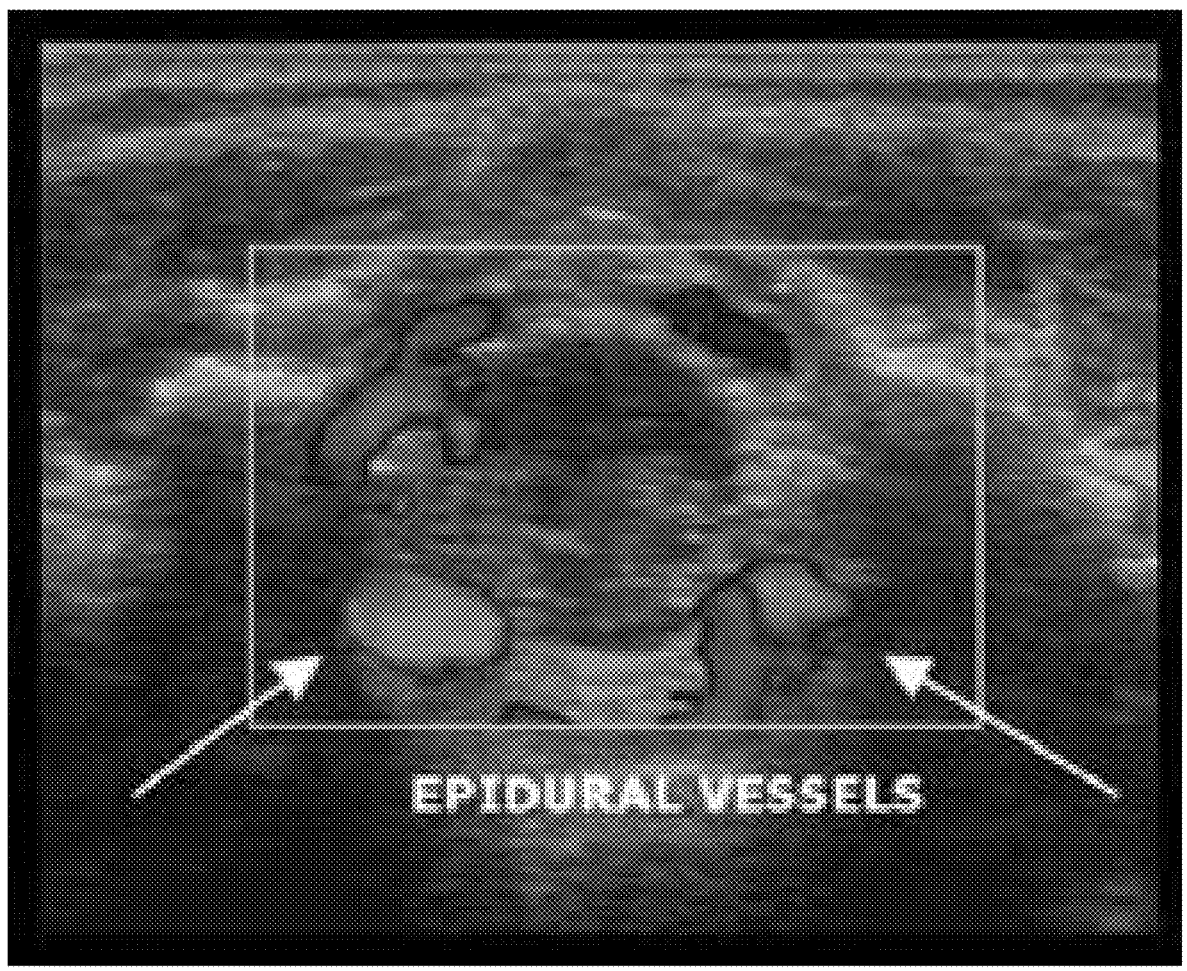
FIG. 16 depicts the transverse view of the spinal canal and the epidural vessels with Doppler effects, in accordance with certain embodiments of the present disclosure.

FIG. 16 depicts the transverse view of the spinal canal 1600 and the epidural vessels with Doppler effects, in accordance with certain embodiments of the present disclosure. The epidural vessels surrounding the spinal canal may be detected using ultrasound. The vessels may then be avoided by the practitioner in order to extract a clean cerebral spinal fluid sample. Other embodiments are also possible.

Figure 17:
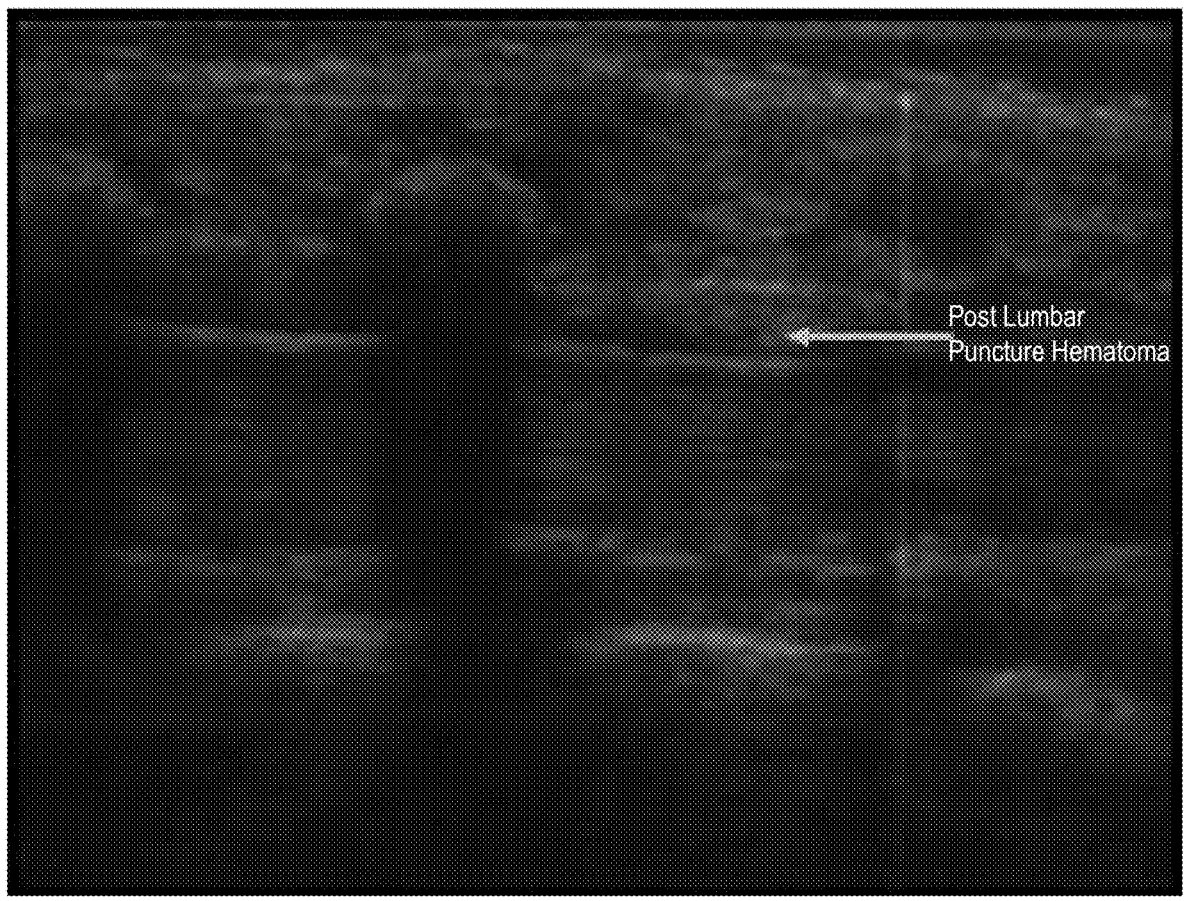
FIG. 17 depicts a midsagittal view of the L3 and L4 vertebral interspace after a failed lumbar puncture.

FIG. 17 depicts a photograph 1700 of a midsagittal view of the L3 and L4 vertebral interspace after a failed lumbar puncture. In particular, the white arrow within the photograph 1700 is located at the level of an echogenic epidural collection consistent with a hematoma that is compressing the dural sac. In some embodiments, an additional unanticipated benefit of sonography for lumbar puncture procedures may include site reevaluation. In particular, when the first attempt is unsuccessful or grossly bloody, the clinician can easily reevaluate the site using ultrasound to determine if a significant hematoma has developed (as shown in photograph 1700). Studies have shown that a repeat lumbar puncture even with direct visualization under sonography is very low when a large epidural hematoma. Accordingly, if a hematoma is present, the lumbar puncture operation can be postponed or other options may be explored.

While the above embodiments described a device for calibrating a safe depth for a needle, it is also possible to calculate the desired depth based on the weight of the patent. One possible example of a pre-calibrated needle with marking indicating depths or lengths and indicating weight ranges is described below with respect to FIG. 18.

Figure 18:
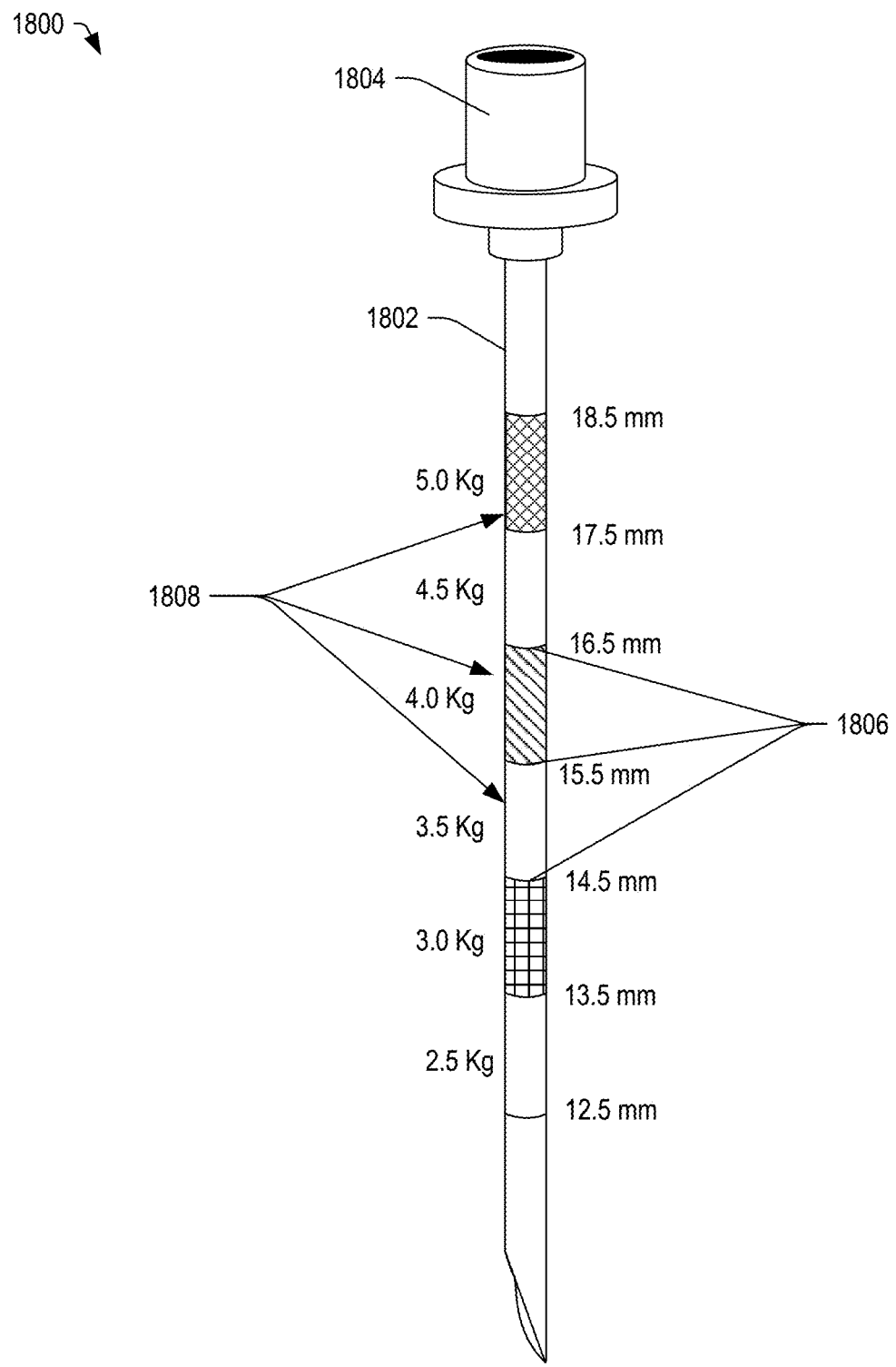
FIG. 18 depicts a needle assembly including calibration markings, in accordance with certain embodiments of the present disclosure.

FIG. 18 depicts a needle assembly 1800 including calibration markings for weight and length, in accordance with certain embodiments of the present disclosure. The needle assembly 1800 may include a needle 1802 coupled to a connector 1804 configured to couple to a syringe (not shown). In the illustrated example, the needle 1802 may include a plurality of regularly spaced marks 1806 representing measurement units, which marks 1806 may be printed or etched onto the needle 1802. In one embodiment, the marks 1806 may represent ten millimeter increments. Alternatively or in addition, the marks may define weight ranges 1808 corresponding to a range of depths that may be suitable for a patient based on the patient's weight. Other embodiments are also possible.

In conjunction with the devices, systems, and methods described above with respect to FIGS. 1-18, a safe depth may be determined using ultrasonic measurements. The safe depth may refer to a depth to an anterior border of a dural sac at a ninety degree insertion angle. Once the safe depth is determined, the needle may be marked at a length corresponding to the safe depth, either with a skin marker or with a slidable element of the devices of FIGS. 1-3. Alternatively, the needle may be provided with printed or etched markings (FIG. 18), and the user may utilize one or more of the pre-defined markings based on the patient. The needle may then be inserted into the patient at a selected insertion angle to the desired depth (as indicated by the mark on the needle) in order to withdraw cerebral spinal fluid.

In the above discussion of FIGS. 1-17, the disclosure has largely focused on the marking of a needle for a safe depth for the purpose of a lumbar puncture procedure. However, the depth determination technique and the corresponding needle marking technique (and associated device) may be used for lumbar puncture procedures as well as for other medical procedures for which the needle insertion depth is determined. Other embodiments are also possible.

Although the present invention has been described with reference to certain embodiments, workers skilled in the art will recognize that changes may be made in form and detail without departing from the scope of the invention.

What is claimed is:

1. A calibration device comprising:
    a tube having a substantially cylindrical body defining an enclosure and having an open end, the tube including measurement units printed along at least one side; and
    a slidable element releasably coupled to the open end of the cylindrical body and configured to selectively engage a needle and provide a dynamic measurement on the needle.

2. The calibration device of claim 1, wherein at least a portion of the tube is transparent.

3. The calibration device of claim 1, wherein the slidable element is configured to allow the needle to advance into and through a stopper element and into the enclosure.

4. The calibration device of claim 3, wherein the slidable element is configured to couple to the needle and disengage the tube when the needle is withdrawn.

5. The calibration device of claim 1, wherein the slidable element includes a v-shaped cut to facilitate viewing of an insertion site.

6. The calibration device of claim 1, wherein the slidable element marks a selected measurement on the needle.

7. A method comprising:
    determining a safe depth parameter for insertion of a needle;
    determining a location on a needle based on measurement units printed on at least one of the needle or a side of a calibration device, the location corresponding to the safe depth parameter; and
    marking the needle at the location corresponding to the safe depth parameter.

8. The method of claim 7, wherein determining the safe depth parameter includes:
    from a first direction, identifying spinal features of a patient using an ultrasound probe;
    from a second direction, identifying the spinal features of the patient using the ultrasound probe; and
    automatically determining a distance from a skin surface of the patient to an anterior dural border through an interspace of interest based on measurements determined using the ultrasound probe.

9. The method of claim 7, wherein determining the safe depth parameter includes:
    determining a weight of a patient; and
    calculating the safe depth parameter based on the weight.

10. The method of claim 7, wherein:
    the calibration device includes a slidable element configured to receive the needle as the needle is advanced into the calibration device; and marking the needle includes withdrawing the needle with the slidable element fixed at the location corresponding to the safe depth parameter.

11. The method of claim 9, wherein the slidable element includes a v-shaped cut to facilitate viewing of an insertion site.

12. The method of claim 7, wherein marking the needle comprises applying a piece of tape to the needle at the location.

13. The method of claim 7, wherein marking the needle comprises drawing a visible mark on the needle at the location using at least one of a marker or a pen.

14. The method of claim 7, wherein marking the needle comprises scratching the needle at the location.

15. A calibration device comprising:
    a housing;
    an opening extending into the housing and sized to receive a needle;
    calibration marks adjacent to the opening, the calibration marks configured to define a plurality of weight ranges and to define regularly spaced measurement units; and an element configured to secure the needle to allow marking of the needle to a selected length based on the calibration marks.

16. The calibration device of claim 15, wherein the element includes a v-shaped cut to facilitate viewing of an insertion site.

17. The calibration device of claim 15, wherein the housing comprises a cylindrical tube.

18. The calibration device of claim 15, wherein the housing comprises a substantially rectangular prism shape.

19. The calibration device of claim 15, wherein the element comprises a slidable element configured to attach to the needle to mark the needle at the selected length.

20. The calibration device of claim 19, wherein the housing is formed from a translucent material.

\* \* \* \* \*